United States Patent [19]

Gruber

[11] 4,193,395
[45] Mar. 18, 1980

[54] REMOVABLE CAST FOR INTERMEDIATE PHASE ORTHOPEDIC REHABILITATION

[76] Inventor: William A. Gruber, 18 Maple Rd., Wellesley, Mass. 02181

[21] Appl. No.: 936,620

[22] Filed: Aug. 24, 1978

[51] Int. Cl.$^2$ .............................................. A61F 5/04
[52] U.S. Cl. .............................. 128/90; 264/DIG. 30; 428/310
[58] Field of Search ............... 128/83, 83.5, 84 R, 128/85, 87 R, 88, 89 R, 89 A, 90; 264/31, 34, DIG. 30; 428/158, 190, 304, 310; 2/2, 16, 22, 24, 44–45

[56] References Cited

U.S. PATENT DOCUMENTS

| | | | |
|---|---|---|---|
| 2,856,919 | 10/1958 | Murray | 128/90 |
| 2,947,307 | 8/1960 | Hoppe | 128/90 |
| 3,176,685 | 4/1965 | Smarook | 128/90 |
| 3,314,419 | 4/1967 | Quick | 128/90 |
| 3,442,265 | 5/1969 | Malven | 128/90 |
| 3,682,163 | 8/1972 | Plummer | 128/87 R |
| 3,728,206 | 4/1973 | Buese | 128/90 |
| 3,880,155 | 4/1975 | Rosoff | 128/90 |
| 3,976,062 | 8/1976 | Cox | 128/87 R |
| 3,998,219 | 12/1976 | Mercer et al. | 128/89 R |
| 4,006,542 | 2/1977 | Larson | 36/43 |
| 4,006,741 | 2/1977 | Arluck | 128/90 |
| 4,019,505 | 4/1977 | Wartman | 128/90 |
| 4,060,075 | 11/1977 | Blomer et al. | 128/90 |

*Primary Examiner*—Robert W. Michell
*Assistant Examiner*—C. F. Rosenbaum
*Attorney, Agent, or Firm*—Cole, Jensen & Puntigam

[57] ABSTRACT

A cast comprised of an outer layer of casting material composed of epsilon polycapriolactone reinforced by a cotton mesh, an inner cotton stockinette, and a layer of padding material composed of medium to high density closed cell elastic sheet foam having an adhesive bearing surface in contact with the stockinette to adhere thereto and the opposed surface in contact with the outer layer for bonding thereto upon thermoforming of the casting material in situ. The cast is especially suited for usage as a removable monovalve cast incident to intermediate phase orthopedic rehabilitation.

21 Claims, 9 Drawing Figures

FIG. 7
FIG. 8
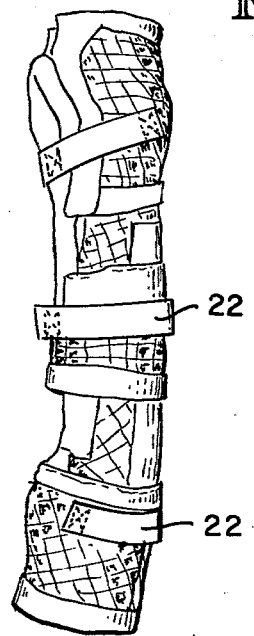
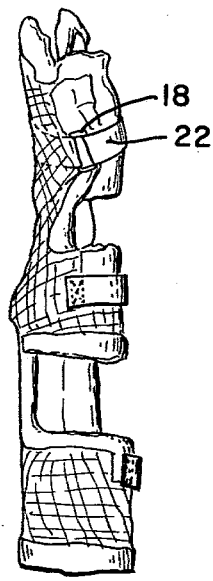
FIG. 9
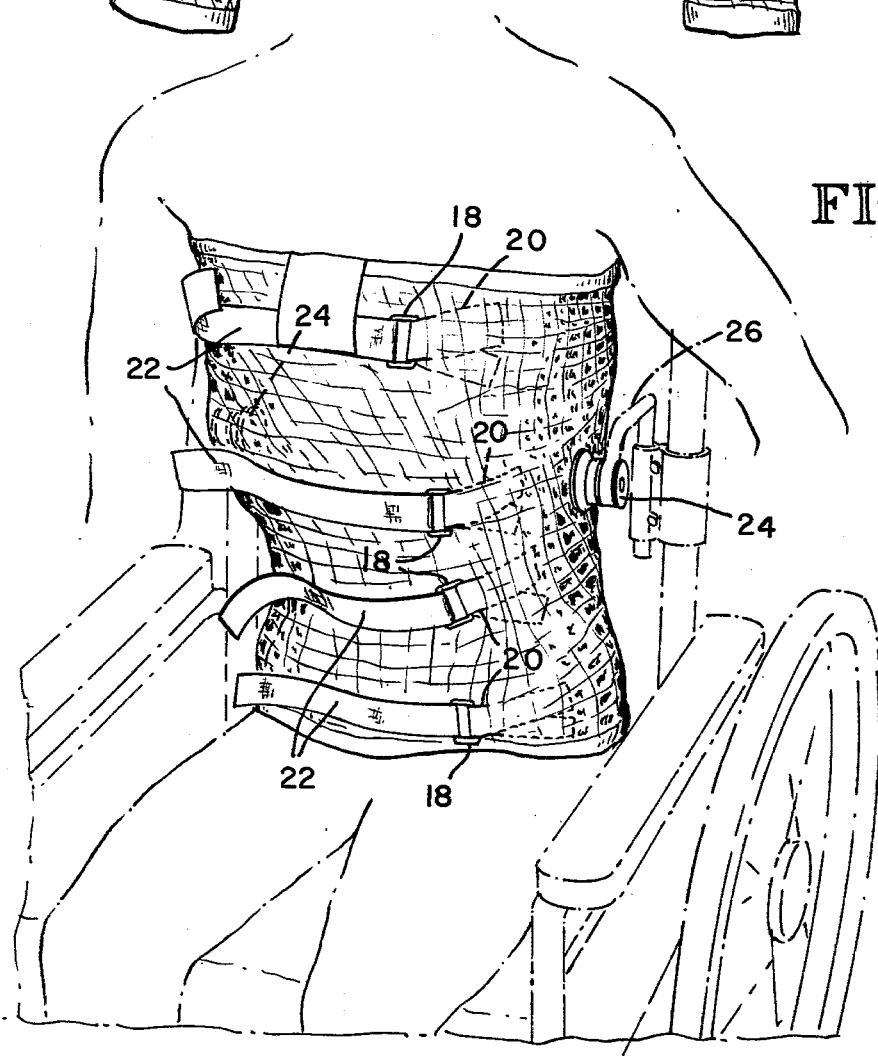

REMOVABLE CAST FOR INTERMEDIATE PHASE ORTHOPEDIC REHABILITATION

BACKGROUND OF THE INVENTION

This invention relates to orthopedic casts and casting methods especially suited for, but not limited to, intermediate phase or orthopedic rehabilitation.

Orthopedic rehabilitation typically occurs in three successive phases: the acute phase immediately following injury or surgery; the intermediate phase during which function is improving; and the chronic phase when function has reached a plateau. The intermediate phase is a variable period extending from approximately 6-8 weeks to approximately 6-8 months after trauma or surgery. The patient population within this phase generally includes those who have achieved preliminary tissue healing, but for whom continued rehabilitation can improve function, and who require removable external fixation devices for mechanical support, prevention of deformity, or maintenance of corrected posture for a limited period.

Plaster casts provide the accepted mode of fixation during the acute phase, whereas orthotic devices are customarily employed during the chronic phase. During the intermediate phase, however, neither plaster nor orthotic devices offer the most effective and economical fixation. Plaster is brittle, possesses low impact and fatigue resistance, cannot be reformed once set, is susceptible to deterioration or damage when exposed to water or urine, and is of excessive weight. In many practical intermediate phase applications, therefore, plaster requires frequent cast replacement, the use of abduction bars, struts and/or heavy reinforcement to prevent cracking, and often results in substantial inconvenience and expense to the patient.

One intermediate phase application which demonstrates some of the drawbacks of plaster is the so-called "bivalve". A bivalve is a removable cast which is formed of two discrete sections adapted to be secured together about the limb or body to provide appropriate fixation. The weight of a plaster bivalve tends to be intolerable, especially to a patient already handicapped by muscle weakness, and may mean the difference between walking and sitting, between patient acceptance and rejection. Furthermore, unlike trauma casts, plaster bivalves require additional labor for lining, padding, petaling, and fitting. These labor costs are multiplied during prolonged use by soiling, breakage, and serial corrections. Curing time adds hidden costs incident to extra hospital days or return visits and so, when examined in this context, plaster bivalves tend to be uneconomical.

Orthotic devices are easily removable and provide variable rigidity and high fatigue resistance, all necessary in the construction of removable intermediate phase rehabilitative devices. Orthotic devices achieve this by using metal for rigidity and leather for flexible cuffs, in combination with sheet plastics. Their structural properties therefore are appropriate for intermediate phase usage; but fabrication requirements are too expensive for the limited use most commonly associated with such usage. More specially, orthotic devices, when fabricated from sheet plastic, require the experience of a trained orthotist, extensive vacuum forming equipment, and frequently a week or more of fabrication time. Modification of such a device during periods of improving function is likewise difficult.

Synthetic casting materials may be utilized to provide lightweight, durable casts in a wide variety of shapes; however, until this invention, synthetic casting materials have been viewed and marketed most commonly as plaster substitutes. As a consequence, splints, rolls, lining, and padding for usage with these casting materials have been designed to appear and function as equivalents to plaster cast components, and these materials have been correspondingly applied like plaster, to make plaster-like casts, primarily during the acute phase.

One thermoplastic material which is suited for usage as an orthopedic casting material is epsilon polycapriolactone; however, this material heretofore has been applied predominately as a plaster substitute in the fabrication of small trauma casts for acute phase application. A woven cotten mesh coated with this material is commercially available in rolls and splints from Hexcel Corporation, Dublin, California as "Hexcelite". At room temperature, epsilon polycapriolactone has a crystalline molecular structure and its surface texture is stiff and hard. When heated in a water bath to about 80° C. (170° F.), it becomes amorphous, plastic, and self-adhesive. Upon cooling, it returns to its original state. This is a repeatable cycle of physical change, without chemical reaction. The aforementioned casting material typically is utilized with a polypropylene stockinette. This type of stockinette, however, tends to be unsatisfactory because it can be allergenic, wets immediately, retains large amounts of water, and dries slowly. When wet, it has a clamy, distinctly unpleasant feeling next to the skin. Additionally, the aforementioned casting material commonly is utilized with different types of padding materials, such as green foam rolls, or "Reston" foam sheets, which are disposed between it and the stockinette. Neither of these padding materials is completely satisfactory. The green foam rolls are composed of 1/16th inch thick open cell polypropylene foam which is thin and very compressible. Although perhaps adequate for simple casts, even in multiple layers, it does not provide good protection under localizers or walking casts, where there is heavy cast pressure. Furthermore, the foam is not self-adherent and multiple layers often are needed for padding. When a cast is bivalved, therefore, these layers come apart and recoil into lumps under the lining. "Reston" foam sheets are composed of a ⅛ inch thick open cell sheet foam, which has good padding properties and is representative of a wide variety of open cell medical foam products available for padding. Open cell foam construction, however, has significant disadvantages in long term cast use in that the open cells break down under prolonged shear forces, and tend to retain water, urine, stool and skin debris.

SUMMARY OF THE INVENTION

This invention provides an orthopedic cast which is especially suited for but not limited to removable intermediate phase rehabilitation usage. The cast is comprised of a thermoplastic casting material, preferably reinforced epsilon polycapriolactone, an inner stockinette or other suitable lining material and an intermediate layer of padding material, preferably medium to high density closed cell elastic sheet foam having an adhesive bearing surface in contact with the stockinette for bonding thereto. Upon thermoforming of the casting material in situ, the casting material is bonded to the opposite surface of the sheet foam to form a laminated cast structure.

This invention also provides a method for making an orthopedic cast by applying a stockinette or inner lining to a portion of the body, applying the aforementioned sheet foam about the stockinette with the adhesive bearing surface thereof in contact with the stockinette, applying a layer of the aforementioned casting materials about the sheet foam while heated to its thermoforming temperature, conforming the casting material and the sheet foam to the contour of the body portion in situ, and thereafter allowing the casting material to cool. Elastic bandage compression by firm wrapping of the cast with elastic bandages soaked in cold water may be utilized to provide close molding to body contours and blending of the casting material reinforcement in situ to form a structurally strong laminate composed of castng material/padding/lining.

According to further aspects of this invention, a removable monovalve cast and process for making it are provided. As used herein, the term "monovalve" refers to a cast which, following thermoforming, is cut in situ along only one side, the portion of the cast opposite the cut being sufficiently flexible to act as a hinge to permit removal of the cast by opening of the cast at the cut and parking of the adjacent portions of the cast so as to bend them about the opposite cast portion. The preferred casting material is particularly suited for fabrication of monovalves or other removable fixation devices, although it may be utilized to form other types of casts or splints. Of particular significance in this regard is that the preferred casting material may be utilized to provide orthopedic casts or external fixation devices of variable rigidity wherein one or more portions are sufficiently rigid to provide adequate structural support, while other portions are sufficiently flexible to allow removal of the cast, or to provide resilient support when in place on a patient. With the preferred casting material, this may be accomplished by applying one or more splits composed of the preferred casting material in the outer layer along with rolls thereof and thermoforming both in situ so as to increase the thickness and hence the rigidity of the cast in those areas in which rigid support is desired. The preferred casting material also possesses sufficient flexibility that the cast obtained may be formed as a monovalve without application of such splints.

The preferred padding material also is significant with respect to removable orthopedic casts or fixative devices in that it provides an adhesive bond with the stockinette. Thus, the stockinette can be cut and removed along with the casting material and padding as a permanent inner lining and does not recoil or form lumps when cut.

Among the advantages of the preferred casting material
(a) Lightweight: requires less exertion from musculoskeletally handicapped patients and those caring for them.
(b) Water Resistant: resists structural deterioration from soiling and spillage, and is easily cleaned.
(c) Easily Applied: minimizes requirements on physician's and patient's time.
(d) Thermoplastic: may be heat reformed to correct pressure areas, allows sectional fabrication, and allows serial correction of deformities.
(e) Variable Rigidity: allows both rigid and flexible areas of a cast to be fabricated from the same material.
(f) High Fatigue Resistance: prevents fatigue failure of flexible components.
(g) High Impact Resistance: prevents structural deterioration from repeated impacts over prolonged use.
(h) Minimal Plastic Deformation: resists structural deformation due to plastic flow under sustained loads for prolonged periods.

Among the advantages of the preferred padding material are:
(a) Closed cell: prevents accumulation of skin debris, urine, stool and food spillage, and provides thermal protection during application.
(b) Medium to High Density: provides adequate cushioning of compressive loads and resists deformation under shear loads.
(c) Elastic: can be stretched to conform closely to irregular body contours.
(d) Adhesive: bonds to the stockinette lining, producing a lining/padding/casting material laminate.
(e) Sheet foam: provides uniform thickness over large body surfaces.

These and other features, objects and advantages of the present invention will become apparent from the detailed description and claims to follow taken in conjunction with the accompanying drawings in which like parts bear like reference numerals.

BRIEF DESCRIPTION OF THE DRAWINGS

FIGS. 7 and 8 are perspective views of a long arm monovalve cast formed of the FIG. 1 laminate;

FIG. 9 is a perspective view of a removable monovalve thoracic suspension orthosis formed of the FIG. 1 laminate.

DETAILED DESCRIPTION OF THE DRAWINGS

Figure 1:
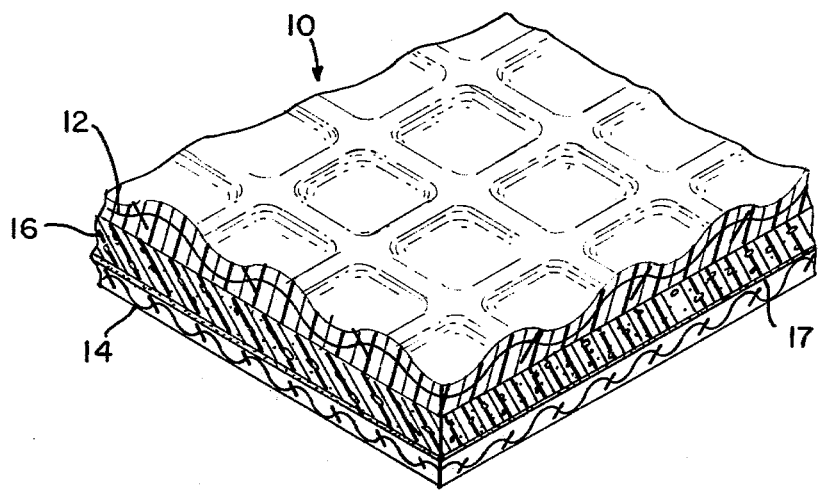
FIG. 1 is a fragmentary perspective view of a laminate embodying the present invention.

Referring first to FIG. 1, a laminate embodying the present invention is comprised of an outer layer (generally referenced 10) of casting material composed of epsilon polycapriolactone reinforced by a woven cloth mesh 12. An inner cotton stockinette 14 of conventional design surrounds the limb or body portion subject to fixation. An intermediate layer of padding material 16 is bonded between layer 10 and stockinette 14. The padding material is composed of a medium to high density closed cell elastic sheet foam having one surface coated with a layer of adhesive 17. The sheet foam is disposed with layer 17 in contact with stockinette 14 and the opposite surface thereof in contact with layer 10. The latter surface is bonded to the casting material during thermoforming, as will be described, to form a laminate structure. A preferred casting material suitable for usage in the present invention is available from Hexcel Corporation of Dublin, California as "Hexcelite." A preferred padding material suitable for usage in the present invention is available from Rolyan Medical Products of Menomonee Falls, Wisconsin as Stock No. A291-2. This padding material should have a sheet thickness of ⅛ to ¼ inch which, in most practical applications, is sufficient to cushion the course pattern of the preferred casting material and provide thermal insulation to the patient during thermofoaming.

In an exemplary application of the FIG. 1 laminate to fabricate a monovalve cast to be described further hereinafter, an inner cotton stockinette is applied to the limb or body portion and extends well beyond the boundaries of the cast for patient protection. This stockinette is later discarded when the cast is removed. A second outer cotton stockinette, which will constitute the permanent inner lining of the cast upon removal, is applied about the inner stockinette and is stretched tightly to eliminate wrinkles. Relief of anatomic pressure areas or bony prominences may be accomplished at this time by conventional cast padding applied to the inner stockinette as needed.

The preferred sheet foam padding material is now applied about the other stockinette. The sheet foam is stretched tightly about the outer stockinette to conform it to any surface irregularities present, with its adhesive surface in contact therewith. Following circumferential wrapping, the sheet foam will be partially overlapped with each convolution adhered to the adjacent inner convolution thereof. A second layer of sheet foam may be similarly applied over bony prominences for additional protection. It is important that the sheet be applied so that no gaps are created between adjacent layers or convolutions to ensure adequate thermal protection.

The preferred casting material is applied about the sheet foam after being heated to its thermoforming temperature in a water bath at a temperature of about 80° C. (170° F.). Splints composed of the preferred casting material may be applied to vary rigidity by increasing the thickness of certain cast areas. They are applied first, next to the sheet foam, in all areas where structural rigidity is required. This technique minimizes heat transfer to the patient because rapid exposure to air of all the splint surfaces rapidly cools the water bath; yet the casting material remains sufficiently elastic to remain workable for an acceptable length of time. Rolls of casting material are applied sparingly, adding only two to three circumferential layers about the splints to form the cuff and hinge areas. The cast is now thermoformed and conformed to body contours in situ while the casting material is still sufficiently warm to achieve adequate molding and firm bonding between layers. In monovalve cast fabrications, appropriate closure devices may be applied to the cast at this point.

Elastic bandage compression may be applied to the outer surface of the cast to provide close molding to body contours and blending of the cotton mesh. Elastic bandages soaked in cold water are wrapped around the completed cast while it is still warm to provide adequate molding necessary for total contact devices and a compressive force that bonds mesh 12 and the preferred casting material into a solid sheet, with a subsequent marked increase in structural strength. This process, of course, also traps heat near the skin; however, complete enclosure of the casted area with sheet foam padding provides adequate thermal protection. When set, the cast is cut along one side and opened thereat to remove it from the limb or body portion, whereupon the cast outlines may be trimmed and the cut edges petalled with moleskin. The cast now is refitted on the patient, closed and is reformed by selective heat application as needed to provide correct fit.

Figure 5:
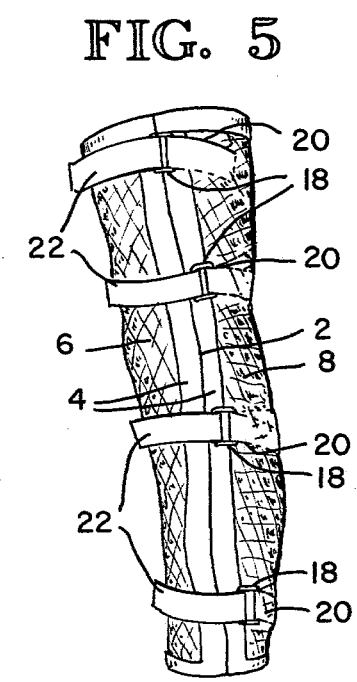
FIGS. 5 and 6 are perspective views of a removable monovalve leg cast formed of the FIG. 1 laminate.
Figure 6:
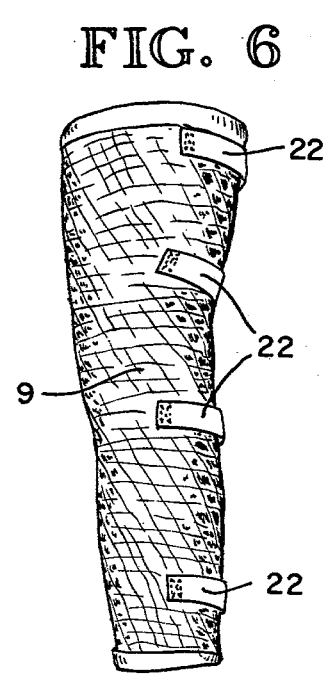

The FIG. 1 laminate is particularly suited for usage in a removable monovalue cast. Several exemplary monovalue cast designs embodying the FIG. 1 laminate are illustrated in FIGS. 2-9. Referring to FIGS. 5 and 6, a full leg removable monovalve cast includes a single cut 2 which is made in situ following thermoforming and extends the length of the cast through all layers thereof. This cut forms two abutting edges which may be encased by appropriate padding material 4. The cast obtained is thus made up of two cast sections (referenced 6 and 8) which are joined together by a common cast portion (referenced 9 in FIG. 6) which is sufficiently flexible to permit sections 6 and 8 to be spread apart, commencing at their abutting edges, for removal of the cast structure from the body portion to be supported, in this instance, the leg. The remaining cast designs illustrated include generally similar parts and may be fabricated following the aforementioned process.

Figure 2:
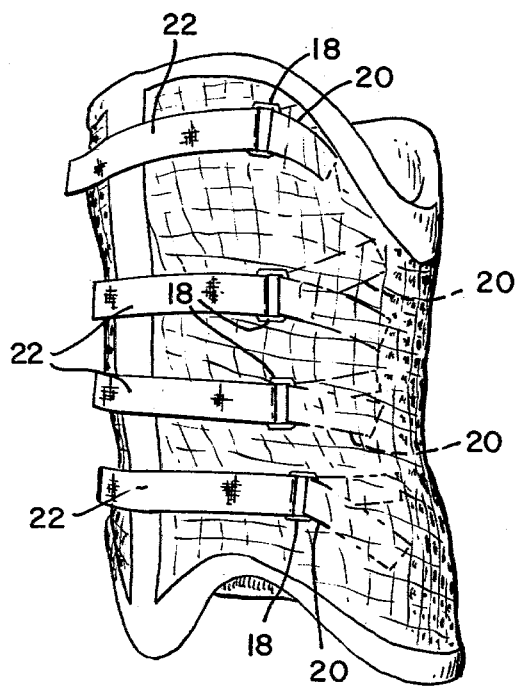
FIG. 2 is a perspective view of a removable monovalve body jacket formed of the FIG. 1 laminate.
Figure 3:
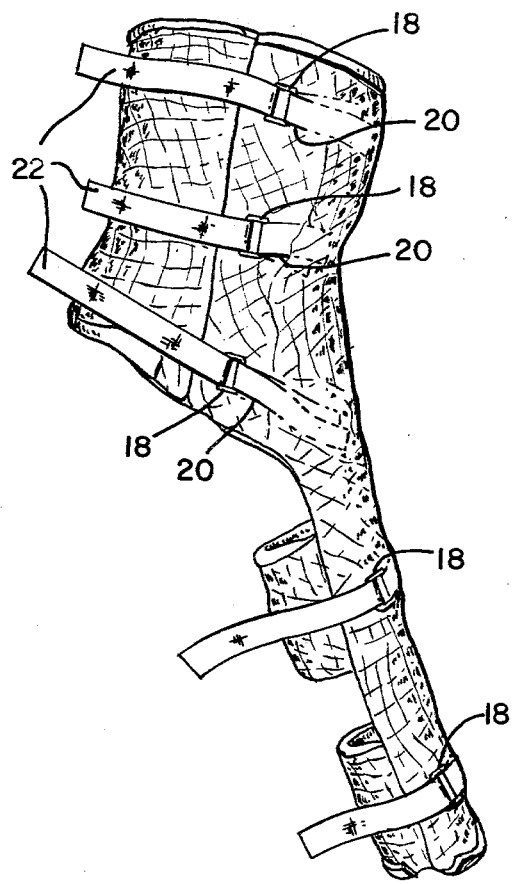
FIG. 3 is a perspective view of a removable monovalve pelvic obliquity spica formed of the FIG. 1 laminate.
Figure 4:
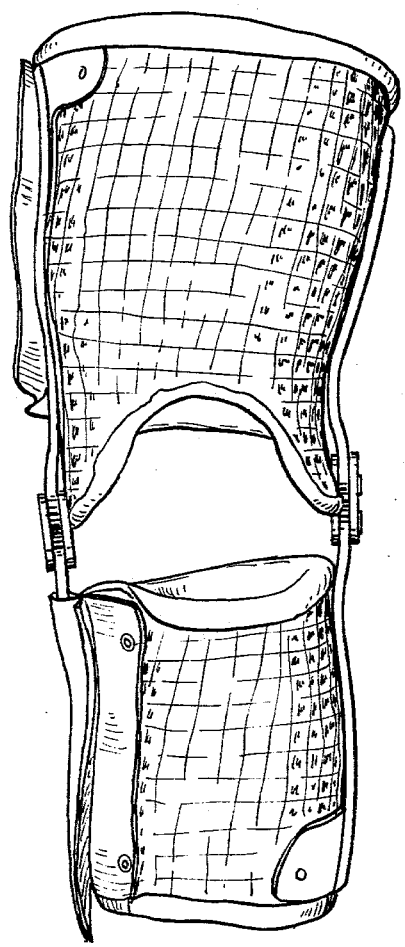
FIG. 4 is a perspective view of a knee brace formed of the FIG. 1 laminate.

Jacket and spica monovalue designs such as those illustrated in FIGS. 2 and 3, respectively, involving the torso require specific techniques to improve closure of the monovalue anteriorly. Ample belly and breast pads should be used to relieve the compression exerted by elastic bandage compression. To prevent pinching of the skin during closure, a thick strip of felt is inserted down the anterior midline between the two layers of stockinette. This will produce an exterior rise in the casting material where the monovalve cut is planned and, when the cut is made down the middle of this rise, the resulting cut edges should be everted to prevent pinching. Folded splints are used along this rise to provide thick cut edges that butt together, rather than overlapping, at closure.

Of particular significance is that a removable monovalve cast embodying the FIG. 1 laminate is sufficiently flexible that, unlike a plaster cast, it may be opened, removed from the patient, refitted to the patient, and closed, without cracking or failure. Common cast portion 9 acts like a hinge and, during opening and closing of the monovalve, flexes to an extent necessary to permit the cast sections to be spread apart or allowed to come together, respectively.

A closure assembly adapted to secure two monovalve cast sections together with their edges in abutting relation also is illustrated in FIGS. 5 and 6. Multiple closure assemblies may be used to secure sections 6 and 8 together at spaced apart locations. Each closure assembly includes a D-ring 18 which is secured to one section of the monovalve by a V-strap 20 formed of the preferred casting material. Strap 20 is applied to the outer cast layer and bonded thereto in situ during the aforementioned fabrication process. A Velcro strap 22 is secured by a generally similar D-ring and V-strap not shown to the other section of the monovalve. Strap 22 is of sufficient length that it may be looped between the D-rings and secured to effect and maintain closure of the two monovalve sections as shown. The remaining cast designs illustrated include generally similar closure assemblies, in which corresponding parts are referenced with the same reference numerals.

In-vitro structural tests utilized bivalved localizers which were fabricated according to this invention and embedded in a plaster base from the waist down. The occipital and shoulder portions of the posterior halves were loaded with 75 lbs. (30 kg) in vertical compression. The anterior halves were unloaded controls. The observation period was five months. No significant plastic deformation of either portion of the posterior halves was observed.

In-vivo test utilized scoliosis as a deformity which could be accurately measured over a prolonged period to determine if deformation and loss of correction had occurred. In-vivo evaluation utilized pre-operative solid localizers which were fabricated according to this invention and applied to five patients. Curve correction and casting were carried out on a localizer frame in the conventional manner and standing AP films were obtained. After a period averating twenty-two days, repeat films were obtained and, based upon a comparison with the original films, it was determined that the cast had held correction. Additional in-vivo evaluation of removable casts according to this invention involved ten patients fused for idiopathic scoliosis. All had right thoracic, left lumbar curves averaging T5 to L3. According to a pre-existing protocol, all were fused without instrumentation. They were, therefore, entirely dependant on external fixation for maintenance of correction. All spent six months in a plaster localizer, followed by six months in a removable body jacket, such as that illustrated in FIG. 2 hereof, extending from the sternal notch to just above the symphysis pubis. On the basis of a comparison of standing AP roentgenograms taken at six months and twelve months, it was determined that the jacket had held correction within acceptable limits. Patients with an average major curve of 34.8 exhibited an average loss of correction of 0.8° and a maximum loss of 4°.

In-vitro testing of impact resistance utilized solid leg casts such as that illustrated in FIGS. 5 and 6, which were subjected to 100 high speed impacts on a right angle concrete edge, and compressive impact of 700 Kg across the cylindrical shape of the cast. Delamination of the casting/padding/stockinette occured although no disintegration of the preferred casting material mesh was observed.

Several exemplary external fixation devices embodying the FIG. 1 laminate are illustrated in FIGS. 2–9. These devices are illustrative but not limiting of practical applications of the FIG. 1 laminate.

REMOVABLE BODY JACKET (FIG. 2)

Many patients require a removable body jacket for a period of time sufficiently brief that it is difficult to justify the cost and fabrication requirements of orthotic sheet plastics. The FIG. 2 jacket provides torso enclosure to provide mechanical support and maintenance of corrected posture in patients with spinal disorders. The jacket can be fabricated using six inch splints and rolls composed of the preferred casting material. The splints are placed in three layers over each iliac crest followed by three layers vertically in the mid-axillary lines. If the jacket extends to the sternal notch, two layers are placed anteriorly and posteriorly at this level. Folded splints are placed in the anterior midline as described above. Two to four six-inch rolls of the preferred casting material, depending on patient size, are then wrapped circumferentially.

The FIG. 2 jacket is structurally equivalent to a jacket fabricated of conventional orthotic materials in its ability to maintain correction of spinal deformity. The fabrication requirements of the FIG. 2 jacket, however, provide significant economic advantages over conventional orthotic materials. The latter commonly include sheet plastics which are formed by vacuum forming techniques wherein a negative and a positive plaster mold, skilled labor, extensive equipment and usually one or two weeks of time are required. The FIG. 2 jacket, however, can be fabricated in approximately 90 minutes, and is immediately available to the patient. Cost of materials and labor needed to fabricate the FIG. 2 jacket is substantially less than that of a conventional jacket of equivalent size.

PELVIC OBLIQUITY SPICAS (FIG. 3)

Fixed pelvic obliquity is a complex problem involving muscle imbalance fascial contracture, and deformity of the lumbosacral spine and hip joints. Surgery is usually required, but an important adjunct is external fixation for prolonged periods. Plaster spica bivalves attempt to hold correction by maintaining the legs in abduction, but frequently the pelvis shifts inside the cast despite leg position. The properties of the FIG. 1 laminate provide a cast design which maintains correction by rigidly holding the pelvis instead of the legs and therefore controls pelvic tilt independently of leg position. This design is generally similar to the girdle of the Milwaukee brace, which has demonstrated the effectiveness of front closure combined with deep iliac molding in stabilizing the bony pelvis.

Fabrication of the FIG. 3 spica is accomplished with the patient on a fracture table with the feet in stirrups. Traction is applied to the abducted leg until the pelvis is level. The abducted leg is allowed to swing wide, temporarily increasing the windblown appearance. The torso position is then applied, with emphasis on deep molding at the waist to fix the iliac crests. Traction is then applied to the previously abducted leg, and it is brought into its corrected position of neutral. The opposite leg is swung into abduction, but the iliac crests are now blocked from swinging with it. The leg portions are added in the usual manner, with thick lateral ribs added for additional rigidity. Care must be taken during application of the leg portions so that the hinge in the posterior midline remains only two to three layers thick, or the monovalve will not open easily. Because control is exerted at the pelvis, the decision to leave one leg free is made on the basis of this hip deformity. In cases of severe spasticity, additional care must be taken so that padding is adequate at the iliac crests. Where both legs are included, no abduction bar is necessary, but the junction of the legs to the hips must be cut wide anteriorly to facilitate placement of the patient in the cast. Accommodations to subcutaneous fat atrophy at the waist is made by trimming back the midline cut in small increments.

INTERIM KNEE ORTHOSIS (FIG. 4)

Surgery or trauma to the knee frequently requires many months of rehabilitation before a plateau of function is reached. During this period, the size of the thigh and the level of function are changing. Orthoses, when needed, are used for limited activity, for a limited time. They need not be fabricated to withstand the high levels of activity required of athletic braces, or the prolonged use of a permanent device. A variety of brace designs have been advocated to meet the needs of patients during this period of rehabilitation. A typical design which can be fabricated from the FIG. 1 laminate is the Iowa Knee Orthosis of FIG. 4.

THORACIC SUSPENSION ORTHOSIS (FIG. 9)

A total contact jacket fabrication of the FIG. 1 laminate and fitted with two opposed lateral lugs 24 (one not shown) to suspend it from wheelchair brackets 26 is illustrated in FIG. 9. This design is generally similar to the Vitrithane TSO developed at Newington Children's Hospital, Newington, CT. It may be used to provide orthopedic rehabilitation incident to collapsing paralytic kypho-scoliosis, ischial decubiti, or pelvic obliquity.

FIGS. 5-8 illustrate additional designs embodying the FIG. 1 laminate; namely, leg cast (FIGS. 5 and 6) and long arm cast (FIGS. 7 and 8). Additional applications of the present invention not illustrated are: shoulder abduction devices; temporary prosthesis; dynamic night supports; and shoe, cylinder, gaiter, short arm, gauntlet, hip spica and shoulder spica casts.

Although one preferred embodiment of the present invention and several practical applications thereof have been illustrated and described herein, variations will become apparent to one of ordinary skill in the art. Accordingly, the invention is not to be limited to the specific embodiment or applications illustrated and described herein, and the true scope and spirit of the invention are to be determined by reference to the appended claims.

The embodiments of the invention in which an exclusive property or privilege is claimed are defined as follows.

1. A removable orthoedic cast, comprising: a sectional cast structure made up of two cast sections joined together by a common cast portion, said cast sections terminating in respective edges which may be positioned adjacent one another to enclose said cast structure about a body portion to be supported, said common cast portion being sufficiently flexible to permit said sections to be spread apart at their edges for removal of said cast structure from the body portion, said cast structure being composed of an outer layer of thermoplastic casing material, an inner layer of lining material, and an intermediate layer of padding material bonded to said outer and inner layers.

2. The cast of claim 1, wherein said casting material is constituted by reinforced epsilon polycapriolactone, and said padding material is constituted by medium to high density closed cell elastic sheet foam.

3. The cast of claim 1, wherein said casting material is constituted by reinforced epsilon polycapriolactone.

4. The cast of claim 1, wherein said padding material is constituted by medium to high density closed cell elastic sheet foam.

5. The cast of claims 1, 2 or 3, including at least one splint composed of said casting material and bonded in said outer layer to increase the thickness of said cast structure at a predetermined location.

6. The cast of claims 2 or 4, wherein said sheet foam includes means for adhesively bonding to said inner layer.

7. The cast of claim 6, wherein said bonding means include a layer of adhesive coated on one surface of said sheet foam overlying said inner layer.

8. The cast of claims 2 or 3, wherein said casting material includes a woven cottom mesh embedded in said epsilon polycapriolactone as reinforcement.

9. The cast of claim 1, wherein said inner layer includes a cotton stockinette.

10. The cast of claim 1, including means connected to said sections adjacent their edges for securing said sections in a position enclosing the body portion with their edges in abutting relationship.

11. An orthopedic cast structure, comprising: a layer of casting material composed of reinforced epsilon polycapriolactone; a layer of lining material; and an intermediate layer of padding material composed of medium to high density closed cell elastic sheet foam bonded to said casting material layer and said lining material layer.

12. The structure of claim 11, wherein said intermediate layer includes means for adhesively bonding to said lining material layer.

13. The structure of claim 12, wherein said bonding means include a layer of adhesive coated on one surface of said sheet foam adjacent said lining material layer.

14. The structure of claim 11, wherein said lining material layer includes a cotton stockinette.

15. The structure of claim 11, wherein said casting material includes a woven cotton mesh embedded in said epsilon polycapriolactone as reinforcement.

16. A method of forming a removable orthopedic cast, comprising the steps of: forming a cast structure composed of an outer layer of thermoplastic casting material, an inner layer of lining material, and an intermediate layer of padding material bonded to said outer and inner layers enclosed about a body portion to be supported; conforming the cast structure to the contour of the body portion in situ; and effecting a single cut the length of the conformed cast structure opposite a portion thereof which is sufficiently flexible to permit the cast structure to be opened at the cut for removal from the body portion.

17. The method of claim 16, wherein the cast structure is formed by applying an inner layer of lining material to a portion of a body, applying an intermediate layer of padding material composed of a medium to high density closed cell elastic sheet foam to the inner layer while bonding the intermediate layer thereto, applying an outer layer of casting material composed of reinforced epsilon polycapriolactone to the intermediate layer, and wherein the cast structure is conformed to the contour of the body portion by thermoforming in situ while bonding the intermediate layer to the outer layer.

18. The method of claim 17, including forming said outer layer of varying thickness to control rigidity of the cast by applying a splint composed of said casting material to the intermediate layer and thermoforming the splint in situ.

19. A removable orthopedic cast formed by the process of: forming a cast structure composed of an outer layer of thermoplastic casting material, an inner layer of lining material, and an intermediate layer of padding material bonded to said outer and inner layer enclosed about a body portion to be supported; conforming the cast structure to the contour of the body portion in situ; and effecting a single cut the length of the conformed cast structure opposite a portion thereof which is sufficiently flexible to permit the cast structure to be opened at the cut for removal from the body portion.

20. The cast of claim 19, wherein the cast structure is formed by applying an inner layer of lining material to a portion of a body, applying an intermediate layer of padding material composed of a medium to high density closed cell elastic sheet foam to the inner layer while bonding the intermediate layer thereto, applying an outer layer of casting material composed of reinforced epsilon polycapriolactone to the intermediate layer, and wherein the cast structure is conformed to the contour of the body portion by thermoforming in situ while bonding the intermediate layer to the outer layer.

21. The cast of claim 20, wherein the process includes forming said outer layer of varying thickness to control rigidity of the cast by applying a splint composed of said casting material to the intermediate layer and thermoforming the splint in situ.

* * * * *